(12) United States Patent
Bhandari et al.

(10) Patent No.: US 10,400,204 B2
(45) Date of Patent: Sep. 3, 2019

(54) RESERVOIR FOR FOOD WASTE RECYCLING APPLIANCE

(71) Applicant: WHIRLPOOL CORPORATION, Benton Harbor, MI (US)

(72) Inventors: Akshay Bhandari, Pune (IN); Thomas L. Burger, Laporte, IN (US); Rachel Maghas, Kalamazoo, MI (US)

(73) Assignee: Whirlpool Corporation, Benton Harbor, MI (US)

( * ) Notice: Subject to any disclaimer, the term of this patent is extended or adjusted under 35 U.S.C. 154(b) by 176 days.

(21) Appl. No.: 15/337,430

(22) Filed: Oct. 28, 2016

(65) Prior Publication Data

US 2018/0119080 A1 May 3, 2018

(51) Int. Cl.
*B01D 46/00* (2006.01)
*C05F 17/02* (2006.01)
*C12M 1/00* (2006.01)

(52) U.S. Cl.
CPC ......... *C12M 23/02* (2013.01); *B01D 46/0045* (2013.01); *C05F 17/02* (2013.01); *C05F 17/0258* (2013.01); *C12M 29/04* (2013.01); *Y02P 20/145* (2015.11); *Y02W 30/43* (2015.05)

(58) Field of Classification Search
CPC ..... Y02W 30/43; Y02P 20/145; C12M 23/02; C12M 29/04; B01D 46/0045; C05F 17/02; C05F 17/0258
See application file for complete search history.

(56) References Cited

U.S. PATENT DOCUMENTS

| 244,000 | A | | 7/1881 | Townsend | |
|---|---|---|---|---|---|
| 5,587,320 | A | * | 12/1996 | Shindo | ...................... A61L 9/16 435/290.1 |
| 6,845,527 | B1 | | 1/2005 | Kohn | |
| 7,018,831 | B2 | | 3/2006 | Gitt | |
| 7,735,761 | B2 | | 6/2010 | Koh | |
| 2004/0040597 | A1 | | 3/2004 | Cheng | |
| 2011/0207218 | A1 | * | 8/2011 | Staheli | ................ B01F 3/04241 435/394 |
| 2017/0260108 | A1 | | 9/2017 | Koh | |

FOREIGN PATENT DOCUMENTS

| DE | 2836151 A1 | 2/1980 |
|---|---|---|
| EP | 0501028 A1 | 9/1992 |
| EP | 3216777 A1 | 9/2017 |
| GB | 2494192 A | 3/2013 |
| WO | 9913172 A1 | 3/1999 |

OTHER PUBLICATIONS

European Search Report for Counterpart EP17198418.0, dated Feb. 28, 2018.

* cited by examiner

Primary Examiner — William H. Beisner
Assistant Examiner — Danielle B Henkel
(74) *Attorney, Agent, or Firm* — McGarry Bair PC

(57) ABSTRACT

The disclosure relates to a food waste recycling appliance having a hollow reservoir which can collect liquid generated during a cycle of operation, drain the collected liquid, and provide an air flow path for the removal of odors.

20 Claims, 6 Drawing Sheets

RESERVOIR FOR FOOD WASTE RECYCLING APPLIANCE

BACKGROUND

Food waste recycling appliances are known to implement a food recycling cycle for biologically and chemically decomposing organic material into homemade fertilizer for use as a fertilizer and soil amendment. The food recycling cycle can be implemented in a bin by providing water, heat and aeration to the food waste, and can require a period of time for completion. During this period of time, water can condense in the appliance and be collected in a reservoir. Odors may also exist within the reservoir.

BRIEF SUMMARY

In one aspect, a liquid reservoir for a food waste recycling appliance that generates liquid during a recycling operation comprises a hollow, generally U-shaped body formed of first and second arm portions joined by a web portion wherein the first and second arm portions and the web portion define an opening, a liquid inlet at a distal end of the first arm portion configured to connect to a source of liquid in a food waste recycling appliance, an air inlet near the distal end of the first arm portion, and an air outlet near a distal end of the second arm portion. The air outlet is configured to connect to a driver to cause air to move from the air inlet through the first arm portion, the web portion, and the second arm portion to the air outlet.

In another aspect, a food waste recycling appliance comprises a liquid reservoir formed of a hollow, generally U-shaped body having first and second arm portions joined by a web portion wherein the first and second arm portions and the web portion define an opening, a food waste container wherein the opening is disposed over the food waste container, a liquid inlet at a distal end of the first arm portion connected to a source of liquid in the food waste recycling appliance, an air inlet near the distal end of the first arm portion; an air outlet near a distal end of the second arm portion and connected to a fan to draw air out of the U-shaped body, and a filter downstream of the fan to treat air exiting the U-shaped body. The fan causes air to move from the air inlet through the first arm portion, the web portion, and the second arm portion to the air outlet where it is treated at the filter.

DETAILED DESCRIPTION

Figure 1:
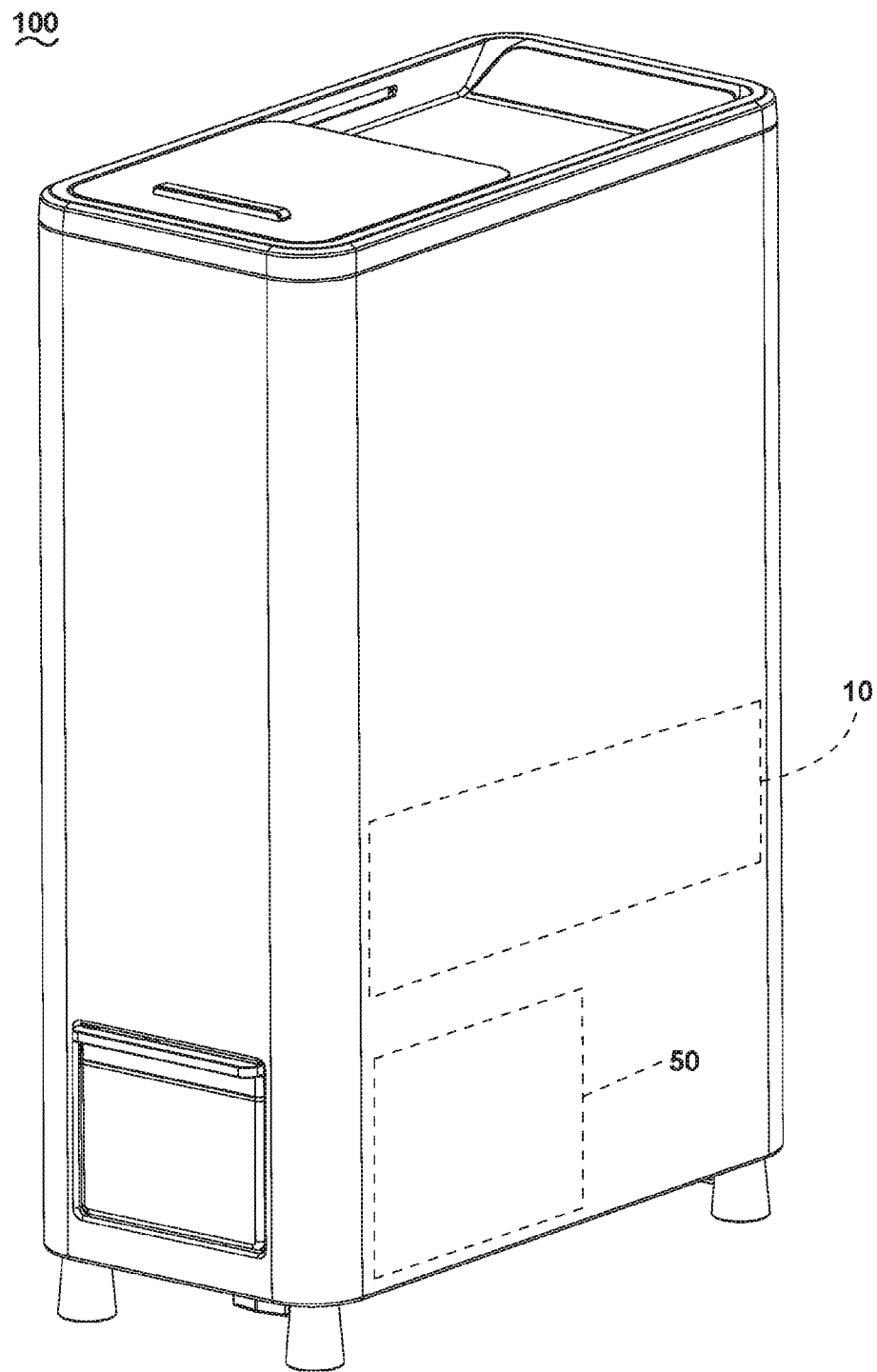
FIG. 1 is a schematic isometric view of a food waste recycling appliance.

FIG. 1 illustrates a schematic view of a food waste recycling appliance 100 for transforming organic material into homemade fertilizer by way of a food recycling cycle of operation. While a "food waste recycling appliance" is described, embodiments of the invention can be equally applicable for similar devices, such as composters or food recyclers or biological waste digesters. The food waste recycling appliance 100 can include a liquid reservoir 10 in accord with the invention, and an output bin 50 typically disposed beneath the liquid reservoir 10.

Figure 2:
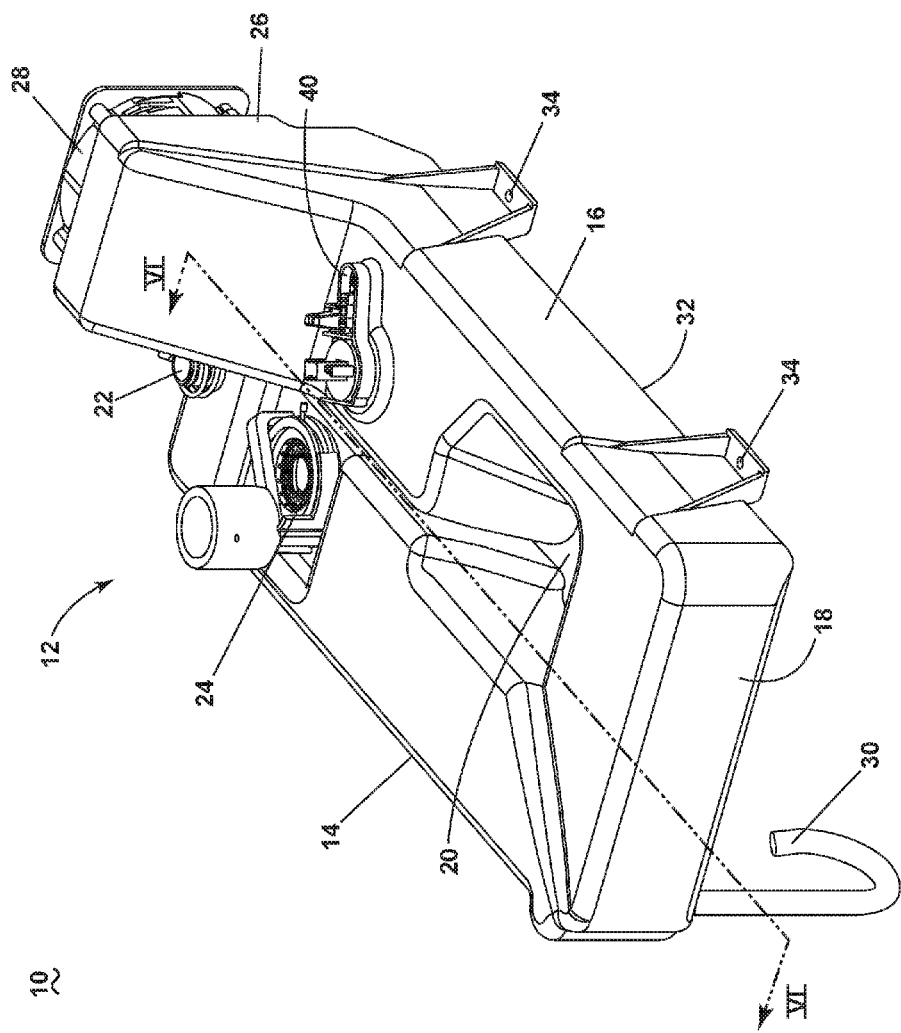
FIG. 2 is an isometric view of a liquid reservoir in the food waste recycling appliance of FIG. 1.

FIG. 2 illustrates an isometric view of the liquid reservoir 10 in the food waste recycling appliance 100 of FIG. 1. The liquid reservoir 10 comprises a hollow, generally U-shaped body 12 having a first arm portion 14 joined to a second arm portion 16 by a web portion 18. Together, the arm portions 14, 16 and web portion 18 define an opening 20. The opening 20 is located so as to be above the output bin 50 in the food waste recycling appliance 100, and dimensioned to enable products from other mechanisms in the food waste recycling appliance 100 to pass through to the output bin 50. A liquid and air inlet 22 can be provided at a distal end of the first arm portion 14 and can be connected to a source of liquid in the appliance 100. In addition, an air inlet 24 can be provided near the distal end of the first arm portion 14, and an air outlet 26 can be provided near the distal end of the second arm portion 16. Further, the portions 14, 16, 18 can have a contiguous bottom wall 32, and a drain outlet 30 can be disposed on the bottom wall 32 near a junction of the web portion 18 and one of the first or second arm portions 14, 16. The drain outlet 30 may be open and unrestricted, or it preferably has a valve or the like to independently control the flow of liquid therethrough. The reservoir 10 can also contain a plurality of legs 34 adapted to mount the reservoir to a frame in the food waste recycling appliance 100. A liquid level sensor 40 can be disposed in the reservoir 10 to measure the level of liquid in the reservoir. Preferably, liquid level sensor 40 is mounted in one of the first or second arm portions 14, 16, and may extend through an upper wall to enable connection to a controller (not shown).

Figure 3:
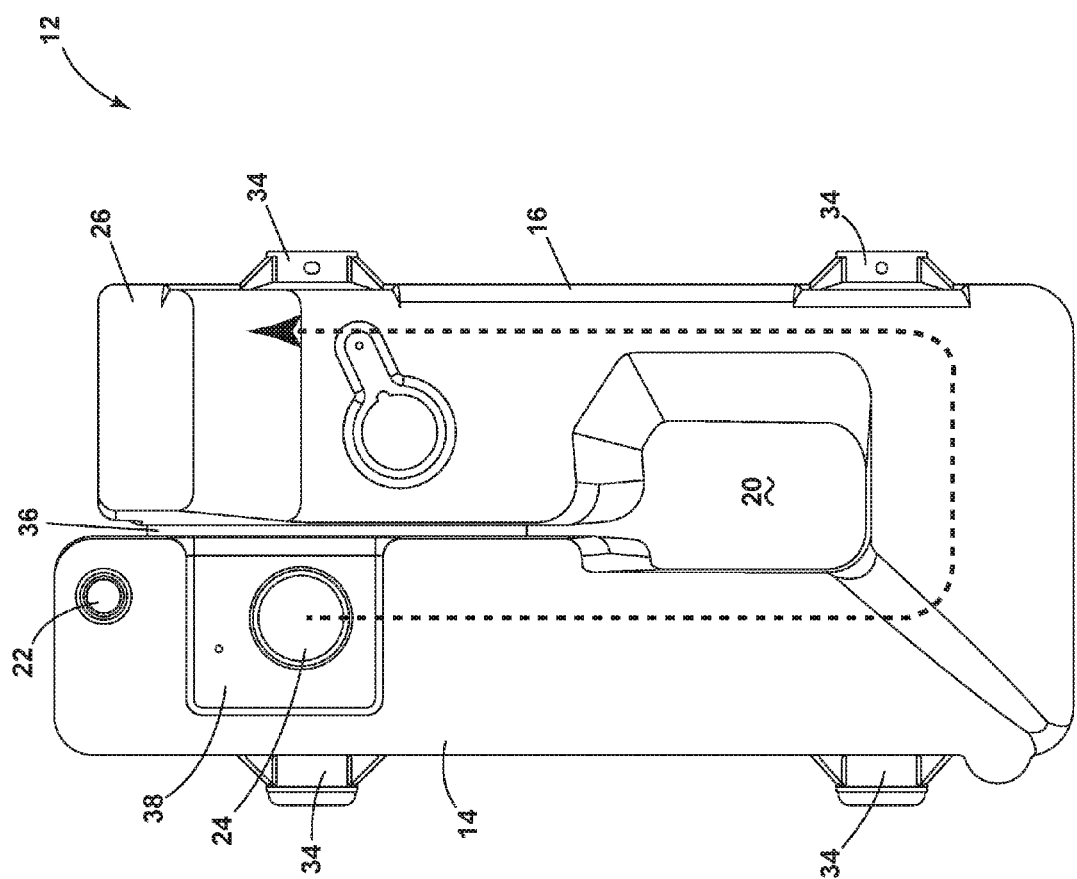
FIG. 3 is a top view of the liquid reservoir of FIG. 2.

Looking now also at the top view of the liquid reservoir 10 in FIG. 3, the distal ends of the first and second arm portions 14, 16 can be joined by a connecting rib 36. Additionally, the air inlet 24 can be positioned within a recessed area 38 adjacent to and opening to the connecting rib 36, as shown. Preferably, the connecting rib 36 is sloped toward the opening 20.

Figure 4:
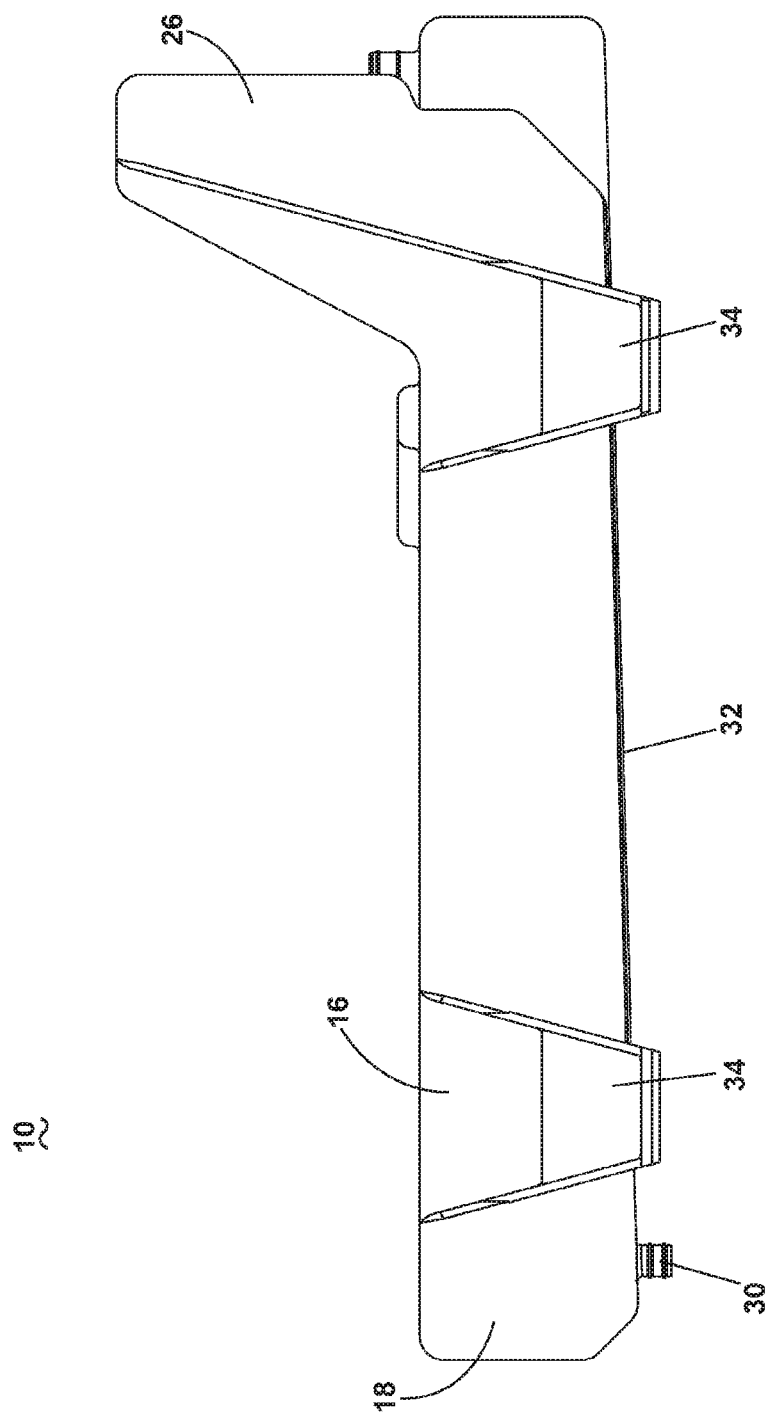
FIG. 4 is a side view of the liquid reservoir of FIG. 2.
Figure 5:
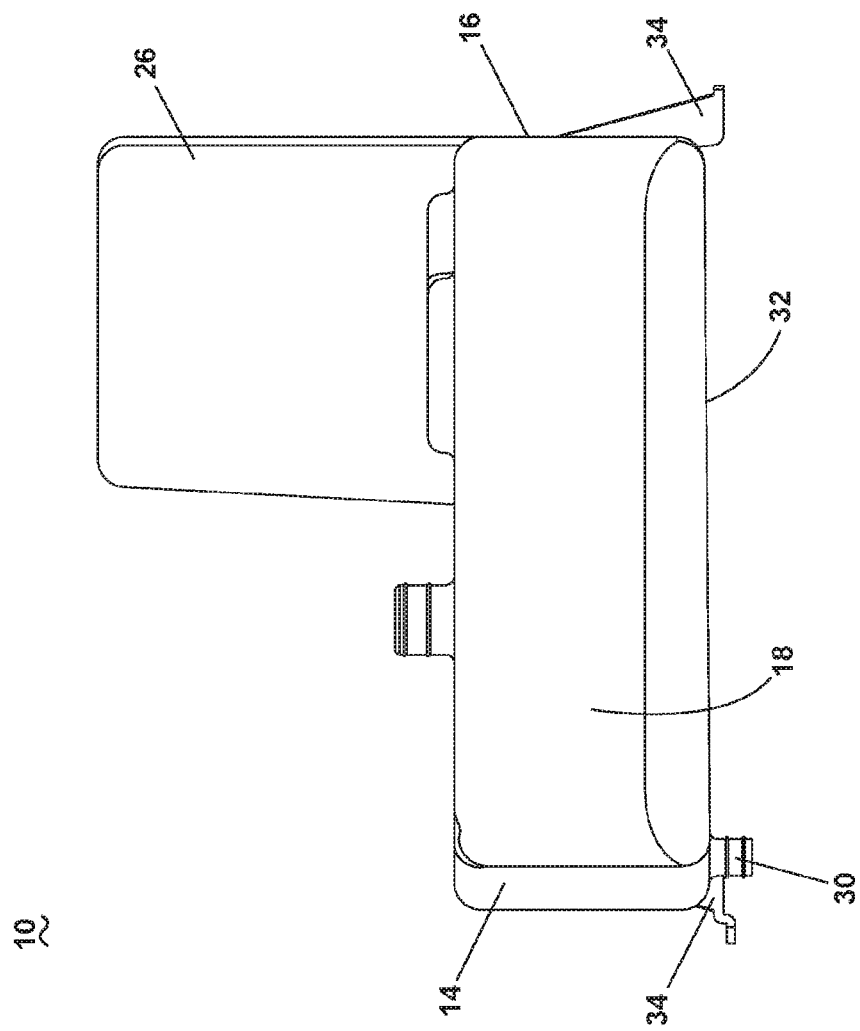
FIG. 5 is a front view of the liquid reservoir of FIG. 2.

FIGS. 4 and 5 illustrate a side view and front view, respectively, of the liquid reservoir 10. The bottom wall 32 can be sloped relative to the legs 34 along the length of at least one of the arm portions 16, 18 as seen in FIG. 4. The bottom wall 32 can also be sloped relative to the legs 34 along the width of the web portion 18 as seen in FIG. 5, such that the bottom wall 32 can slope in two directions toward the drain outlet 30.

Figure 6:
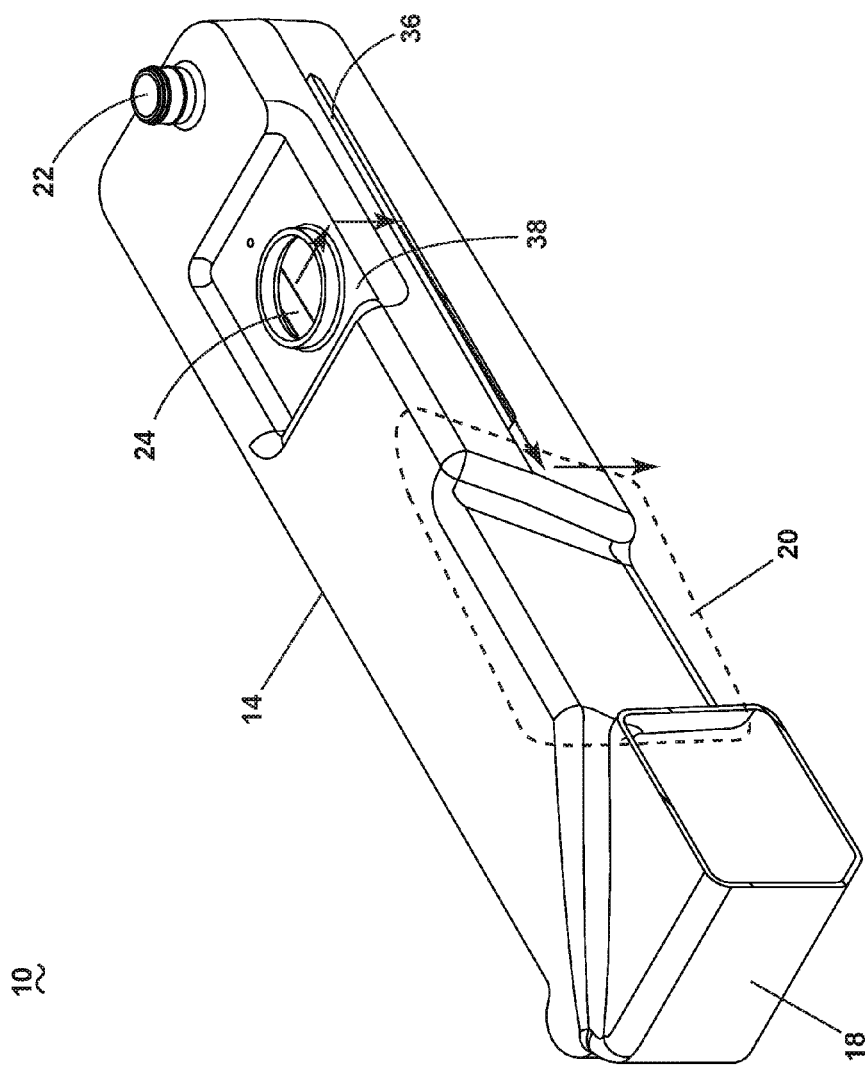
FIG. 6 is an isometric sectional view of the liquid reservoir of FIG. 2 taken along the line 6-6.

FIG. 6 illustrates an isometric sectional view of the liquid reservoir 10 from FIG. 2 taken along line 6-6. The recessed area 38 can be positioned adjacent and above the connecting rib 36, and the rib 36 can extend to the opening 20 as shown.

In a standard cycle of operation, liquid generated within the food recycling appliance 100 can flow through the liquid/air inlet 22 into the body 12 of the reservoir 10, downward along the sloped bottom wall 32 (FIGS. 4 and 5) toward the drain outlet 30, and then exit the reservoir 10 if or when the drain outlet is open. It can be appreciated that the liquid level sensor 40 (FIG. 2) can monitor the amount of liquid contained in the reservoir 10. In the event of any overflow of liquid out of the air inlet 24, the liquid can flow along the recessed area 38 to the connecting rib 36 and then to the opening 20 as shown in FIG. 6. The opening 20 can be disposed above the food waste container 50 as shown in FIG. 1 in order to safely collect any overflowing liquid from the reservoir 10, and thus any electrical components mounted to the exterior of the reservoir 10 can be protected from exposure to moisture. It can also be appreciated that the connecting rib 36 can provide additional structural strength to the reservoir 10.

It is contemplated that a driver 28 (FIG. 2), such as a suction fan, can be connected to the air outlet 26 and cause air to be drawn out of the body 12 of the liquid reservoir 10. Air can enter the reservoir 10 through either or both of the inlets 22 and 24, move within the first arm portion 14, the web portion 18, and the second arm portion 16, and then exit the reservoir 10 through the air outlet 26; an exemplary air flow path is shown in FIG. 3. It can be appreciated that the surface of liquid contained in all portions of the reservoir 10 can be in contact with this air flow such that any odors present within the liquid and elsewhere inside the reservoir 10 may be removed while the driver 28 is in operation. It is further contemplated that a filter (not shown) may be positioned within the food waste recycling appliance 100, outside of the reservoir 10 and downstream of the driver 28, in order to treat the air flowing out of the reservoir 10. Such treatment may include removal of odors.

The material used for the first and second arm portions 14, 16 and the web portion 18 may be any material suitable for the environmental conditions found in a food waste recycling device, such as metal or plastic, and it is contemplated that these portions may be formed of blow molded plastic. In addition, the legs 34 can support the first and second arm portions 14, 16 and the web portion 18 in the food waste recycling appliance 100. Any suitable attachment method may be used to attach the legs 34 to the interior of the appliance 100, such as screws.

To the extent not already described, the different features and structures of the various embodiments can be used in combination with each other as desired. That one feature cannot be illustrated in all of the embodiments is not meant to be construed that it cannot be, but is done for brevity of description. Thus, the various features of the different embodiments can be mixed and matched as desired to form new embodiments, whether or not the new embodiments are expressly described. Combinations or permutations of features described herein are covered by this disclosure.

This written description uses examples to disclose embodiments of the invention, and also to enable any person skilled in the art to practice embodiments of the invention, including making and using any devices or systems and performing any incorporated methods. The patentable scope of the invention is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A liquid reservoir for a food waste recycling appliance, with a fan, that generates liquid during a recycling operation, the liquid reservoir comprising:

a generally U-shaped body, with a hollow interior, having first and second arm portions joined by a web portion, each of the first and second arm portions having a proximal end at the web portion and a distal end remotely spaced from the web portion, with at least some of the first arm, second arm, and web portions at least partially bounding an interstitial space exterior of the U-shaped body;

a food waste through opening defined by an exterior surface of the U-shaped body and passing through the interstitial space;

a liquid inlet located in the distal end of the first arm portion configured to fluidly connect to a source of liquid in a food waste recycling appliance to the hollow interior;

an air inlet fluidly coupled to the hollow interior and located in the distal end of one of the first and second arm portions; and an air outlet fluidly coupled to the hollow interior and located in the distal end of the other of the first and second arm portions;

wherein the air outlet is configured to connect to the fan to cause air to move from the air inlet through the hollow interior along the first arm portion, the web portion, and the second arm portion to the air outlet.

2. The liquid reservoir of claim 1 further comprising a drain outlet near a junction of the web portion and one of the first or second arm portions.

3. The liquid reservoir of claim 2 wherein the first and second arm portions and the web portion have a contiguous bottom wall and a drain outlet is in the bottom wall at the junction of the web portion and one of the first or second arm portions.

4. The liquid reservoir of claim 3 wherein the bottom wall slopes toward the drain outlet.

5. The liquid reservoir of claim 4 wherein the bottom wall of the web portion and the bottom wall of the one of the first or second arm portions both slope toward the drain outlet.

6. The liquid reservoir of claim 4 further comprising legs to support the first and second arm portions and the web portion in the food waste recycling appliance, and the slope of the bottom wall is relative to the legs.

7. The liquid reservoir of claim 1 further comprising a rib joining the first arm portion to the second arm portion near the distal ends of the first and second arm portions.

8. The liquid reservoir of claim 7 further comprising a recessed area around the air inlet and opening toward the rib wherein liquid overflowing through the air inlet will flow to the rib and then to the opening along the rib.

9. The liquid reservoir of claim 1 further comprising a liquid level sensor disposed in one of the first or second arm portions.

10. The liquid reservoir of claim 1 wherein the first and second arm portions and the web portion are formed of blow molded plastic.

11. A food waste recycling appliance comprising:
    a liquid reservoir comprising:
        a generally U-shaped body, with a hollow interior, having first and second arm portions joined by a web portion, each of the first and second arm portions having a proximal end at the web portion and a distal end remotely spaced from the web portion, with at least some of the first arm, second arm, and web portions at least partially bounding an interstitial space exterior of the U-shaped body;
        a food waste through opening defined by an exterior surface of the U-shaped body, passing through the interstitial space;
        a liquid inlet fluidly connected to the hollow interior and located in the distal end of the first arm portion and connected to a source of liquid in the food waste recycling appliance;
        an air inlet fluidly connected to the hollow interior and located in the distal end of one of the first and second arm portions; and an air outlet fluidly connected to the hollow interior and located in the distal end of the other of the first and second arm portions;

a food waste container located below the food waste through opening of the liquid reservoir;

a fan connected to the air outlet of the liquid reservoir; and a filter downstream of the fan to treat air exiting the hollow, generally U-shaped body;

wherein the fan causes air to move through the generally U-shaped body from the air inlet to the air outlet where it is treated at the filter.

12. The food waste recycling appliance of claim 11, further comprising a drain outlet near a junction of the web portion and one of the first or second arm portions.

13. The food waste recycling appliance of claim 12 wherein the first and second arm portions and the web portion have a contiguous bottom wall and a drain outlet is in the bottom wall at the junction of the web portion and one of the first or second arm portions.

14. The food waste recycling appliance of claim 13 wherein the bottom wall slopes toward the drain outlet.

15. The food waste recycling appliance of claim 14 wherein the bottom wall of the web portion and the bottom wall of the one of the first or second arm portions both slope toward the drain outlet.

16. The food waste recycling appliance of claim 14 further comprising legs to support the first and second arm portions and the web portion in the food waste recycling appliance, and the slope of the bottom wall is relative to the legs.

17. The food waste recycling appliance of claim 11 further comprising a rib joining the first arm portion to the second arm portion near the distal ends of the first and second arm portions.

18. The food waste recycling appliance of claim 17 further comprising a recessed area around the air inlet and opening toward the rib wherein liquid overflowing through the air inlet will flow to the rib and then to the opening along the rib.

19. The food waste recycling appliance of claim 11 further comprising a liquid level sensor disposed in one of the first or second arm portions.

20. The food waste recycling appliance of claim 11 wherein the first and second arm portions and the web portion are formed of blow molded plastic.

* * * * *